United States Patent [19]

Paolino

[11] Plant 4,224

[45] Mar. 14, 1978

[54] ROSE PLANT—MEINUZETEN VARIETY

[75] Inventor: Marie-Louise Paolino, Antibes, France

[73] Assignee: The Conard Pyle Company, West Grove, Pa.

[21] Appl. No.: 779,569

[22] Filed: Mar. 21, 1977

[30] Foreign Application Priority Data

Mar. 24, 1976 Italy ..... 21532 A/76

[51] Int. Cl.[2] ..... A01H 5/00

[52] U.S. Cl. ..... Plt./11

[58] Field of Search ..... Plt./11, 15–17

*Primary Examiner*—Robert E. Bagwill

*Attorney, Agent, or Firm*—Burns, Doane, Swecker & Mathis

[57] ABSTRACT

A rose plant of the Hybrid Tea Class is provided having double flowers which are Saturn red on the inside and ochre yellow on the outside. The seed parent of the new variety resulted from the pollenation of a seedling obtained by the fertilization of the variety MEIalfi by the variety Meifan 00186F with pollen from the variety King's Ransom. The pollen parent of the new variety was the variety Whisky Mac.

15 Drawing Figures

SUMMARY OF THE INVENTION

The object of the present invention is to provide a new variety of rose-plant of the Hybrid Tea Class having double flowers which is distinguished from prior varieties by the following characteristics:

(1) particularly elegant slightly perfumed flowers which are Saturn red on the inside, and ochre yellow on the outside, and (2) a bush growth habit which exhibits staged blossoming which is rapidly remontant.

In view of these characteristics the new variety meets the needs of the horticultural industry and is particularly suited for ornamental use in parks and gardens.

The seed parent of the new variety resulted from the pollenation of a seedling obtained by the fertilization of the variety MEIalfi by the variety Meifan 00186F with pollen from the variety King's Ransom (U.S. Plant Pat. No. 2103). The pollen parent of the new variety was the variety Whisky Mac.

This parentage of the new variety may be expressed as follows:

[(MEIalfi × Meifan 00186F) × KING'S RANSOM] × WHISKY MAC

The seeds resulting from the above pollenation were sown and 525 plantlets were obtained which were physically and biologically different from each other. Selective study resulted in the identification and preservation of the new variety. Extensive testing has confirmed the behavior and productivity of the new variety.

The characteristics and properties of this new variety, obtained as indicated above are strictly transmissible by agamic means, also called "asexual", i.e., by means of vegetative propagation, in particular by grafting an eye. The rose-plant of the new variety has been designated the Meinuzeten variety.

BRIEF DESCRIPTION OF THE DRAWINGS

The accompanying drawings show as nearly true as it is reasonably possible to make the same in a color illustration of this character, typical specimens of the cut flowers and foliage, illustrated in.

Figures 1, 2, 3, 4, 5, 6, 7, 8, 9, 10, 11, 12, 13, 14, 15:
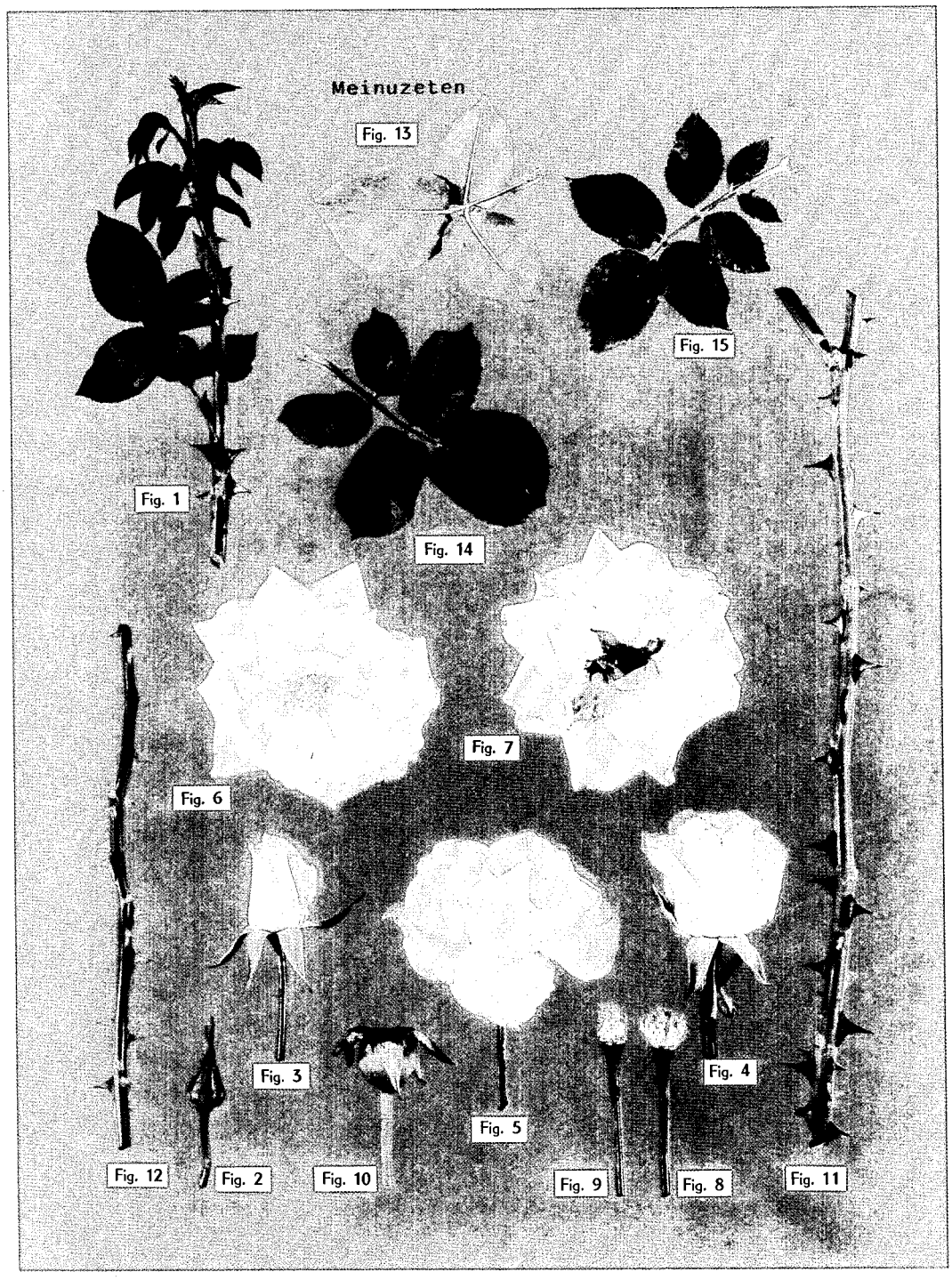
FIG. 1 — a specimen of young shoot.

FIG. '— a specimen of a bud before the opening of the sepals;

FIG. 3 — a specimen of a bud at the opening of the sepals;

FIG. 4 — a specimen of a bud at the opening of the petals;

FIG. 5 — a specimen of a fully open flower;

FIG. 6 — a specimen of a flower in bloom — plan view — obverse;

FIG. 7 — a specimen of a flower in bloom — plan view — reverse;

FIG. 8 — a specimen of a receptacle showing the arrangement of the stamens;

FIG. 9 — a specimen of a receptacle showing the arrangement of the pistils (stamens removed);

FIG. 10 — a specimen of fruit;

FIG. 11 — a specimen of a main branch;

FIG. 12 — a specimen of a floral stem;

FIG. 13 — a specimen of a 3—foliole leaf — under surface;

FIG. 14 — a specimen of a 5—foliole leaf — upper surface; and

FIG. 15 — a specimen of 7—foliole leaf, upper surface.

DETAILED DESCRIPTION OF THE DISCLOSURE

The plant described was grown in the open air in Cannet-des-Maures, Var, France.

The chart used in the identification of the colors is that of the Royal Horticultural Society (R.H.S. Color Chart). The terminology preceding the numbered references proper to this chart, has been added to designate, in common terms, the corresponding colors.

Class: Tea hybrid.

Plant:

*Height.*—1.30 to 1.40 meters.

*Habit.*—Bush.

Branches:

*Color.*—Young stems: light green 146/B (yellow green group) broadly shaded with reddish coloration. Mature wood: bronze green 164/A (yellow green group).

*Thorns.*—Shape: Upper edge: straight. Lower edge: concave. Size: rather large. Quantity: average. Color — on young stems: reddish. On mature wood: greenish pink, then havana brown (common terms).

Leaves:

*Stipules.*—Adnate, pectinated, broad and linear.

*Petiole.*—Obverse: grooved — reddish brown on young foliage, medium green on mature foliage — more or less glandular. Reverse: reddish brown on young foliage, light green on mature foliage, carries some small hooked thorns.

*Folioles.*—Number: most often 3 and 5, also 7. Shape: oval, cordiform base, pointed tip. Denticulation: simple and regular. Texture: coriaceous. General effect: rather ample and dense foliate, half-mat aspect. Color — young foliage: Obverse: dark green 147/A (yellow green group) more or less spotted with reddish coloration. Reverse: light green 147/C (yellow green group) more or less spotted with reddish coloration. Adult foliage: Obverse: dark green 147/A (yellow green group). Reverse: light green 147/C (yellow green group).

INFLORESCENCE

*Number of flowers.*—Generally one flower per stem.

*Peduncle.*—Straight, rigid, generally smooth, broadly spotted with brown-reddish coloration. Length: 6.5 cm.

*Sepals.*—Obverse: tomentose, greenish more or less spotted with reddish coloration; Reverse: light green more or less spotted with reddish coloration. The sepals on the outside have their edges broadly appendiculate and slightly glandular.

*Bud.*—Shape: conical. Length: 3.5 cm. Size: large. Color. — on opening: Obverse: Saturn red 30/B (orange red group) toward the center, capsic red 33/A (orange red group) on the edges. Reverse: Ochre yellow 22/A (yellow orange group) broadly spotted with carmine coloration on the edges.

*Flower.*—Form: first as full cup, then opens into hollow cup with stamens apparent, double flower. Diameter: 10.5 cm. on the average. Color — at the opening. Obverse: Saturn red 30/C (orange red group) toward the center and fire red 33/B (orange red group) on the edges. Reverse: Ochre yellow 22/A (yellow orange group) toward the center and Spanish orange 26/B (orange group) lightly dotted with carmine on the edges. While opening — Obverse: Saturn red 30/C (orange red group) increasingly intense toward the center, and shrimp red 33/C (orange red group) in depth and on edges. Reverse: ochre yellow 22/A (yellow orange group) toward the center and Spanish orange 26/B (orange group) on the edges. When fully open — Obverse: orange 30/D (orange red group) toward the center and shrimp red 33/C (orange red group) in depth and on edges. Reverse: chamois orange 22/B (yellow orange group) toward the center and Spanish orange 26/C (orange group) on the edges. Fragrance: light. Lasting quality: long.

*Corolla.*—Petals — texture: consistent. Shape: tip broadly rounded — base obtuse. The unguis is lemon yellow 14/B (yellow orange group) on the obverse. Number: 30 to 35 including perhaps a false petal and 1 or 2 incomplete petals in the center. Stripping of petals: they detach properly. Stamens — number: 164 on an average. Anthers: normal, yellow, with terminal insertion. Filaments: yellow, irregular heights. Pistils — number: 95 on an average. Stigmas: normal — yellowish. Styles: free — straw with fuchsine tip (common terms), more or less twisted and tomentose, of irregular heights. Receptacle: light green more or less spotted with reddish brown (common terms) coloration. At the dehiscence of anthers when viewed in a longitudinal section, it is narrow and jug shaped.

DEVELOPMENT

*Vegetation.*—Very vigorous.

*Blossoming.*—Very staged and rapidly remontant.

*Capacity to fructify.*—Very slight.

*Resistance to frosts.*—Spring: normal. Winter: normal. To cryptogamic diseases: very good.

I claim:

1. A new and distinct variety of Hybrid Tea rose-plant of vegetative reproduction, characterized by the fact that from the physical point of view, the plant with bronze green mature wood has a bush growth habit, a double flower which is Saturn red on the inside and ochre yellow on the outside, and consistent petals which carry a lemon yellow unguis on the obverse; and from the biological point of view this rose-plant is of vigorous vegetation, exhibits staged blooming which is rapidly remontant, has resistance to cryptogamic diseases, and long lasting flowers having petals which detach properly;

substantially as shown and described.

* * * * *

Meinuzeten